US005686618A

United States Patent [19]

Schneider

[11] Patent Number: 5,686,618
[45] Date of Patent: Nov. 11, 1997

[54] METHOD FOR PREPARING 3-AMINO-2-CHLORO-4-ALKYLPYRIDINE OR-4-ARYLPYRIDINE

[75] Inventor: Heinrich Schneider, Ingelheim am Rhein, Germany

[73] Assignee: Boehringer Ingelheim KG, Ingelheim am Rhein, Germany

[21] Appl. No.: 495,551

[22] PCT Filed: Dec. 1, 1994

[86] PCT No.: PCT/EP94/03988

§ 371 Date: Sep. 11, 1995

§ 102(e) Date: Sep. 11, 1995

[87] PCT Pub. No.: WO95/15314

PCT Pub. Date: Jun. 8, 1995

[30] Foreign Application Priority Data

Dec. 2, 1993 [DE] Germany ............ 43 41 033.2

[51] Int. Cl.⁶ .................................. C07D 213/73

[52] U.S. Cl. .................................. 546/311
[58] Field of Search ........................ 546/311

[56] References Cited

U.S. PATENT DOCUMENTS 5,200,522  4/1993  Grozinger et al. ............ 546/250

FOREIGN PATENT DOCUMENTS 9222531  12/1992  WIPO ............ 546/11

OTHER PUBLICATIONS

Klingsberg, Pyridine and Its Derivative, 1962, pp. 36–39.
Schickh et al., *Chem. Ber.*, 69, 2593 (1936).

*Primary Examiner*—Zinna Northington Davis
*Attorney, Agent, or Firm*—R. P. Raymond; Alan R. Stempel; Mary Ellen Devlin

[57] ABSTRACT

The present invention relates to a new process for preparing 3-amino-2-chloro-4-alkyl- or -4-aryl-pyridines on an industrial scale.

5 Claims, No Drawings

METHOD FOR PREPARING 3-AMINO-2-CHLORO-4-ALKYLPYRIDINE OR-4-ARYLPYRIDINE

CROSS-REFERENCES TO RELATED APPLICATIONS

This application is derived, pursuant to 35 U.S.C. 371, from PCT/EP94/03988, filed Dec. 12, 1994.

The present invention relates to a process for preparing 3-amino-2-chloro-4-alkyl-or 4-aryl-pyridines, particularly for preparing 3-amino-2-chloro-4-$C_{1-3}$-alkylpyridines, or, in particular, for preparing 3-amino-2-chloro-4-methylpyridine, which can be used on an industrial scale.

The above-mentioned alkylpyridines are important starting compounds for the synthesis of 5,11-dihydro-6H-dipyrido-[3,2-b:2',3'-e]diazepines; particular mention should be made of Nevirapin which is effective against HIV infections.

From the prior art there are various possible methods for synthesising 3-amino-2-chloro-4-methylpyridine, for example by catalytic hydrogenation of 2-chloro-3-nitro-4-methyl-pyridine. However, 3-amino-2-chloro-4-methylpyridine is not available in large amounts since it is not possible to chlorinate 3-amino-4-methylpyridine with chlorine on an industrial scale.

According to the invention, a two-step synthesis is proposed, preferably without isolation of the product of the first step, in which the starting compound used is a corresponding 2,6-dichloro-3-amino-4-alkyl or 4-aryl-pyridine, preferably 2,6-dichloro-3-amino-4-methylpyridine. Alternatively, the pyridine derivatives of general formula III may be prepared, again starting from the 3-amino-pyridines of general formula II. The following synthetic scheme illustrates the course of the synthesis:

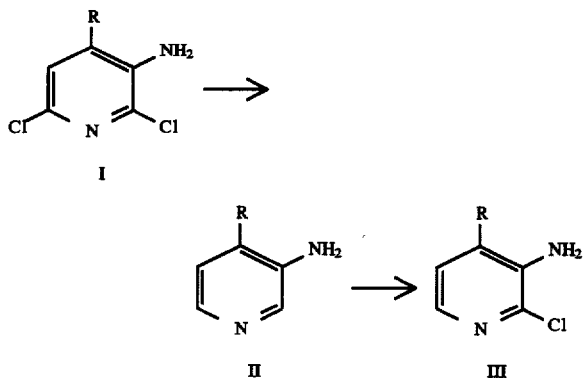

A pyridine derivative of general formula I wherein

R=a $C_{1-8}$-alkyl group, preferably a $C_{1-4}$-alkyl group, most preferably methyl, or R denotes an optionally substituted $C_{3-6}$-cycloalkyl group or R denotes a group of formula

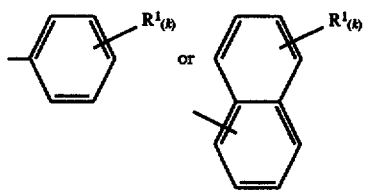

$R^1$ denotes hydrogen, $C_{1-4}$-alkyl (optionally substituted by halogen or hydroxy), nitro, cyano, hydroxy, $C_{1-4}$-alkoxy, $C_{1-4}$-alkoxy-$C_{1-4}$-alkyl, $C_{1-4}$-alkylsulphonyl, halogen, $C_{1-4}$-hydroxyalkyl-sulphonyl, $COOC_{1-4}$-alkyl, $COOC_{1-4}$-alkylphenyl, cyclopropyl, SH, S-$C_{1-4}$-alkyl;

k denotes 1, 2 or 3, preferably 1, is converted in a two-step synthesis, via catalytic dehalogenation to give a derivative of general formula II wherein R is as hereinbefore defined followed by selective chlorination in the 2-position, into a pyridine derivative of general formula III wherein R is as hereinbefore defined.

The alkyl groups used (including those which are constituents of other groups) may be methyl, ethyl, propyl, isopropyl, n-propyl, n-butyl, isobutyl, sec.-butyl and tert.-butyl, unless otherwise specified.

Cycloalkyl generally denotes a saturated cyclic $C_{3-6}$-hydrocarbon group which may optionally be substituted with one or several halogen atoms, a hydroxy group, an alkyl group, preferably methyl, which may be identical or different. Examples include cyclopropyl, cyclobutyl, cyclopentyl, cyclopentenyl, cyclohexyl and cyclohexenyl. Phenyl groups may, for example, be substituted with one or more lower alkyl groups, alkoxy groups, nitro groups, amino groups and/or one or more halogen atoms (which may be identical or different).

The aryl groups may be optionally substituted phenyl or naphthyl groups.

A substituted phenyl group may also, for example, carry one or more of the substituents listed below: $C_{1-6}$-alkyl, $C_{1-6}$-alkoxy, halogen, amino, alkylamino, dialkylamino, $CF_3$, $C_{3-6}$-cycloalkyl, cyano, $NO_2$, COH, COOH, $COOC_{1-4}$-alkyl, cyclopropyl, hydroxy and hydroxymethyl.

Examples of substituted phenyl are as follows: 3-chlorophenyl, 4-chlorophenyl, 3-bromophenyl, 4-bromophenyl, 4-fluorophenyl, 2-chlorophenyl, 2-bromophenyl, 3-fluorophenyl, 2,3-dichlorophenyl, 2-methylphenyl, 4-methylphenyl, 3-ethylphenyl, 4-propylphenyl, 4-isopropylphenyl, 4-butylphenyl, 4-tert-butylphenyl, 4-isobutylphenyl, 4-pentylphenyl, 2,4-dimethylphenyl, 2-trifluoromethylphenyl, 3-trifluoromethyl-phenyl, 4-trifluoromethylphenyl, 2-methoxyphenyl, 4-methoxyphenyl, 3-ethoxyphenyl, 2-propoxyphenyl, 4-butoxyphenyl, 2,4-dimethoxyphenyl and 3,4,5-trimethoxyphenyl.

Alkoxy generally denotes a straight-chained or branched $C_{1-4}$-hydrocarbon group connected via an oxygen atom. Examples include methoxy, ethoxy, propoxy, isopropoxy, butoxy or isobutoxy.

The number of carbon atoms specified relates to the length of the alkyl chain unless otherwise stated.

In the first reaction step the pyridine of general formula I is reacted by catalytic reduction to obtain a dehalogenated pyridine derivative of general formula II. The preferred reducing agents can be inferred from the remainder of the specification and the Examples.

The person skilled in the art is aware that, under the reducing reaction conditions of the reaction step, groups R which are prone to reduction must either be protected or else (deliberate) conversion of the group R must be taken into account when planning the synthesis.

The 3-aminopyridine derivative of general formula II thus formed, wherein R is defined as in I, may be worked up and isolated using conventional methods. However, direct further reaction is recommended, namely chlorination in the 2-position of the pyridine using $HCl/H_2O_2$ in aqueous solution. According to the invention, hydrochloric acid with a concentration of about 20 wt.-% or more is suitable; concentrated hydrochloric acid with a content of about 36 wt.-% is preferred. The concentration of the $H_2O_2$ solution is not critical, but concentrated solutions of about 20–35 wt.-% are preferred. Higher concentrations of $H_2O_2$ are theoretically possible, but it must be borne in mind that highly concentrated $H_2O_2$ solutions constitute a risk owing to the danger of explosions in industrial processes. The reaction is usually carried out at temperatures between 30° and 50° C.

Further processing is carried out by a fractional extraction at different pH levels. After the reaction has ended the pH is adjusted to between −1 and +1 using sodium hydroxide solution or another suitable base and the reaction mixture is extracted with a suitable solvent, preferably with a halohydrocarbon. Suitable solvents are methylene chloride, chloroform and others. Suitable solvents are those which are resistant to the reactants, for example, and are not readily flammable for safety reasons. After the organic phase has been worked up some starting material is recovered. Depending on the substituents in the 4- and 5-positions of the pyridine of general formula III the solubility of the products is reduced, e.g. in the case of the 3-amino-2-chloro-4-aryl-pyridines. These may be isolated directly by precipitating them out of the aqueous phase at pH 7–14. More soluble derivatives, particularly 3-amino-2-chloro-4-alkyl-pyridines are worked up as follows: the aqueous phase is adjusted to a pH of 3.5 to 5, e.g. using a 45 wt.-% sodium hydroxide solution.

The subsequent extraction with a suitable organic solvent, e.g. methylene chloride, followed by conventional working up of the organic phase, yields the desired 3-amino-2-chloro-4-alkylpyridine, preferably the 3-amino-2-chloro-4-methylpyridine.

It is preferable to prepare 4-alkyl-pyridines as they are already used in the manufacture certain drugs.

2,6-Dichloro-3-amino-4-alkylpyridine (preferably R=methyl) is converted into the 3-amino-4-alkylpyridine by catalytic reduction. The preferred reducing agent is hydrogen in the presence of a palladium/carbon catalyst. The preferred solvent is methanol/water.

The 3-amino-4-alkylpyridine, preferably 3-amino-4-methylpyridine, may be worked up and isolated using conventional methods. However, direct further reaction is preferred according to the invention, namely subsequent chlorination in the 2-position using $HCl/H_2O_2$ in aqueous solution.

Further processing is carried out by fractional extraction at different pH levels. After the reaction has ended the pH is adjusted to between −1 and +1 by the addition of a base, preferably sodium hydroxide solution or another suitable base, and the reaction mixture is extracted with a halohydrocarbon. Suitable solvents are methylene chloride, chloroform and others.

After the organic phase has been worked up, the 2,6-dichloro-3-amino-4-alkylpyridine, preferably 2,6-dichloro-3-amino-4-methylpyridine, which is formed as a by-product of chlorination is obtained and this may be used as the starting material once more.

The aqueous phase is adjusted to a pH of 3.5 to 5, for example using a 45 wt.-% sodium hydroxide solution. Subsequent extraction with a suitable organic solvent, e.g. methylene chloride, followed by the usual working up of the organic phase, yields the desired 3-amino-2-chloro-4-alkylpyridine, preferably 3-amino-2-chloro-4-methylpyridine.

Using the process according to the invention it is possible for the first time to produce 3-amino-2-chloropyridines with no substituents in the 6-position on an industrial scale. The substituents in the 4-position or in the 4- and 5-positions may be selected freely, provided that steps are taken to ensure that they will tolerate the reaction conditions chosen.

Starting from 3-amino-pyridines substituted in the 4-position or in the 4- and 5-positions, chlorination by reaction with $HCl/H_2O_2$ is carried out almost exclusively in the 2-position of the pyridine, using the process according to the invention. The reaction conditions are analogous to those described previously.

The starting compounds are either known or may be prepared by simple analogy processes.

The Examples which are described hereinafter illustrate the invention:

EXAMPLE 1

1st Step:
Reduction of 2,6-dichloro-3-amino-4-methylpyridine.

177 kg of 2,6-Dichloro-3-amino-4-methylpyridine are dissolved in 531 liters of methanol and 170 liters of water and mixed with 5 kg of 10% palladium/carbon and reduced with hydrogen gas at 70°–90° C. Then the catalyst is filtered off and the solvent is distilled off until virtual dryness.

2nd Step:
Chlorination of 3-amino-4-methylpyridine

The residue thus obtained from the first step is dissolved by the addition of 250 liters of 36% hydrochloric acid, then a total of 103 liters of 35% $H_2O_2$ are added continuously at a temperature of 34°–45° C. After the reaction has ended the pH is adjusted to between −1 and +1 using sodium hydroxide solution. Extraction is then carried out several times using methylene chloride.

The aqueous phase remaining is then adjusted to a pH between 3.5 and 5 using sodium hydroxide solution. After the addition of 6 kg of sodium sulphite, extraction is carried out several times with methylene chloride. The combined organic phases are evaporated down and worked up.

122.6 kg=86% of theory of the 3-amino-2-chloro-4-methylpyridine are obtained. A further 8.6 kg of product are obtained by working up the mother liquors.

Recovery of 3-amino-2,6-dichloro-4-methylpyridine:

The organic phase of the first extraction of the above-described synthesis is worked up as follows.

The organic phase is mixed with 6 kg of 45% sodium hydroxide solution and 80 liters of water and extracted, the lower organic phase is separated off and the aqueous phase is mixed once more with 25 liters of methylene chloride. From the combined organic phase, after conventional working up, 7.1 kg =4% of theory of 3-amino-2,6-dichloro-4-methylpyridine are obtained, which can be reused in the reaction.

EXAMPLE 2

3-Amino-2-chloro-4-n-propylpyridine

In a 1 liter stirred autoclave 150.0 g of 3-amino-2,6-dichloro-4-n-propylpyridine and 5.0 g of 10% palladium/carbon are suspended in a mixture of 450.0 ml of methanol and 150.0 ml of water and hydrogenated under 3 bars of hydrogen at 50°–70° C. until the uptake of gas has ceased.

The catalyst is filtered off and the resulting solution of 3-amino-4-n-propylpyridine×2 HCl is evaporated down to the residue. 219.5 g of 36–37% hydrochloric acid are added to the residue and over about 3 hours 99.5 g of 30% hydrogen peroxide are added dropwise thereto at 35°–40° C. Stirring is continued for about another 1.5 hours at 40° C., then 97.6 g of 45% sodium hydroxide solution are added at 20°–30° C. and the mixture is extracted three times with 75.0 ml of methylene chloride. From these extracts, 5–15% of dichloro compound can be recovered. The aqueous phase is diluted with 375.0 ml of water and adjusted to pH 12 using about 227.6 g of 45% sodium hydroxide solution.

The crystals precipitated are suction filtered, washed with water and dried.

Mp.: 75°–77° C.

Yield: 98.4 g corresponding to: 78.9% of theory

EXAMPLE 3

3-Amino-2-chloro-4-phenylpyridine

In a 1 liter stirred autoclave 150.0 g of 3-amino-2,6-dichloro-4-phenylpyridine and 15.0 g of 10% palladium/carbon are suspended in a mixture of 450.0 ml of methanol and 150.0 ml of water and hydrogenated under 3 bars of hydrogen at 50°–70° C. until the uptake of gas has ceased.

The catalyst is filtered off and the resulting solution of 3-amino-4-phenylpyridine×2 HCl is evaporated down to the residue. 188.3 g of 36–37% hydrochloric acid are added to the residue and over about 3 hours 85.4 g of 30% hydrogen peroxide are added dropwise thereto at 35°–40° C. Stirring is continued for a further 1.5 hours at 40° C., 83.7 g of 45%. sodium hydroxide solution are added at 20°–30° C. and the mixture is extracted three times, each time with 75.0 ml of methylene chloride. From these extracts, 5–15% dichloro compound can be recovered. The aqueous phase is diluted with 375.0 ml of water and adjusted to pH 7 using about 139.5 g of 45% sodium hydroxide solution.

The crystals precipitated are suction filtered, washed with water and dried.

Mp.: 98°–99° C.

Yield: 102.7 g corresponding to 80.0% of theory.

I claim:

1. A process for preparing 3-amino-2-chloro-4-alkyl-pyridine, wherein the alkyl moiety is of 1 to 3 carbons, which process comprises reacting 3-amino-4-alkyl-pyridine, wherein the alkyl moiety is of 1 to 3 carbons, with $HCl/H_2O_2$ in aqueous solution.

2. A process for preparing 3-amino-2-chloro-4-alkyl-pyridine, wherein the alkyl moiety is of 1 to 3 carbons, which process comprises:

(a) reacting 3-amino-4-alkyl-pyridine, wherein the alkyl moiety is of 1 to 3 carbons, with $HCl/H_2O_2$ in aqueous solution;

(b) adjusting the pH of the reaction medium to between −1 and +1 by the addition of a base, and extracting the by-products into a halohydrocarbon solvent; and, (c) adjusting the pH of the aqueous phase to between 3.5 and 5 by the addition of a base, and isolating the 3-amino-2-chloro-4-alkyl-pyridine so produced by extraction into a halohydrocarbon solvent, followed by evaporation of the solvent; or, in the case of derivatives which are not readily soluble, adjusting the pH of the aqueous phase to between 7 and 14, and directly precipitating the product.

3. The process of claim 2 wherein the halohydrocarbon used for extraction is methylene chloride.

4. A process for preparing 3-amino-2-chloro-4-methyl-pyridine, which process comprises reacting 3-amino-4-methyl-pyridine with $HCl/H_2O_2$ in aqueous solution.

5. A process for preparing 3-amino-2-chloro-4-methyl-pyridine, which process comprises:

(a) reacting 3-amino-4-methyl-pyridine with $HCl/H_2O_2$ in aqueous solution;

(b) adjusting the pH of the reaction medium to between −1 and +1 by the addition of a base, and extracting the 2,6-dichloro-3-amino-4-methylpyridine into methylene chloride; and, (c) adjusting the pH of the aqueous phase to between 3.5 and 5 by the addition of a base, and isolating the 3-amino-2-chloro-4-methyl-pyridine so produced by extraction into methylene chloride, followed by evaporation of the methylene chloride.

* * * * *